United States Patent
Nishi et al.

(10) Patent No.: US 7,785,559 B2
(45) Date of Patent: Aug. 31, 2010

(54) METHOD OF FORMING HYPOBROMOUS ACID IN AQUEOUS SYSTEM

(75) Inventors: Zenichi Nishi, Shiga (JP); Koichi Kudoh, Nara (JP); Naoya Okamoto, Moriyama (JP)

(73) Assignee: Tohzai Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 11/662,120

(22) PCT Filed: Nov. 22, 2004

(86) PCT No.: PCT/JP2004/017354

§ 371 (c)(1),
(2), (4) Date: Jan. 15, 2008

(87) PCT Pub. No.: WO2006/030540

PCT Pub. Date: Mar. 23, 2006

(65) Prior Publication Data

US 2009/0047208 A1    Feb. 19, 2009

(30) Foreign Application Priority Data

Sep. 17, 2004    (JP) .............................. 2004-271943

(51) Int. Cl.
*C01B 7/07*     (2006.01)
*C01B 11/04*    (2006.01)
*C02F 1/76*     (2006.01)
(52) U.S. Cl. ..................... 423/488; 423/473; 210/753
(58) Field of Classification Search ............... 423/488, 423/473; 210/753; A01N 59/00, 59/16; C02F 1/50
See application file for complete search history.

(56) References Cited

U.S. PATENT DOCUMENTS 4,574,084 A    3/1986    Berger (Continued)

FOREIGN PATENT DOCUMENTS

CN    1503763 A    6/2004

(Continued)

OTHER PUBLICATIONS

"Sterilization of Water" Mitsumi Kaneko, Japan Education Center of Environmental Sanitation, Aug. 1997, pp. 125-127—Japanese language original; and—Partial English language translation.

*Primary Examiner*—Jessica L Ward
*Assistant Examiner*—Alexander Polyansky
(74) *Attorney, Agent, or Firm*—The Webb Law Firm

(57) ABSTRACT

A method which especially can safely produce a hypobromous acid or a water-soluble salt thereof, that does not require expensive equipment or the like, does not involve extra work such as pre-mixing or have restrictions such as producing immediately prior to use, and is simple. Further, a method which can efficiently and rapidly form a hypobromous acid or a water-soluble salt thereof which is stable and has high sterilization/anti-microbial effect, and which does not form harmful bromic acid. At least either a hypobromous acid or a water-soluble salt thereof is formed by reacting at least either a hypochlorous acid or a water-soluble salt thereof with a bromide in a liquid to be treated, wherein the at least either hypobromous acid a water-soluble salt thereof is formed by adding a modified chlorite to the liquid to be treated.

4 Claims, 1 Drawing Sheet

U.S. PATENT DOCUMENTS 6,136,205 A    10/2000   Dallmier et al.
7,033,510 B2    4/2006   Cilliers et al.

FOREIGN PATENT DOCUMENTS

| | | | |
|---|---|---|---|
| JP | 60-500572 | | 4/1985 |
| JP | 60-129182 | | 7/1985 |
| JP | 05-213706 | | 8/1993 |
| JP | 11-506139 | | 6/1999 |
| JP | 2001-501869 | | 2/2001 |
| JP | 2002-086155 | | 3/2002 |
| JP | 2004-210701 | * | 7/2004 |
| WO | WO 97/34827 | | 9/1997 |
| WO | WO 0164310 | * | 9/2001 |

* cited by examiner

METHOD OF FORMING HYPOBROMOUS ACID IN AQUEOUS SYSTEM

TECHNICAL FIELD

The present invention relates to a method of forming at least either a hypobromous acid or a water-soluble salt thereof by reacting at least either a hypochlorous acid or a water-soluble salt thereof with a bromide in a liquid to be treated.

BACKGROUND ART

A hypobromous acid or a water-soluble salt thereof can exhibit a high sterilization effect or anti-microbial effect in liquid to be treated having a high pH (e.g. hot spring water from a highly alkaline spring, white water or open-circulating cooling water in a papermaking machine at a pulp and paper mill and the like). Therefore, a hypobromous acid or a water-soluble salt thereof are used as for disinfection or as a slime control agent for such liquid to be treated.

Conventional methods of producing a hypobromous acid or a water-soluble salt thereof include the following reported production methods:

blowing ozone into a solution containing bromide ions to convert the bromide ions to hypobromous acid (refer to Patent Document 1);

adding a hypochlorite and a bromide to a liquid to be treated, whereby the resulting reaction forms a hypobromite (refer to Patent Documents);

making a bromide present in the liquid to be treated, and then adding aqueous peracetic acid or aqueous hydrogen peroxide to form a hypobromite (refer to Patent Document 3); and with a sulfamate compound as a stabilizer, pre-mixing a hypochlorite and a bromide to produce a stable hypobromite (refer to Patent Documents 4 and 5).

Patent Document 1: Japanese Patent Application "kokai" No. 5-213706

Patent Document 2: Japanese Patent Application "kokai" No. 60-129182.

Patent Document 3: Japanese Patent Application "kohyo" No. 2002-86155

Patent Document 4: Japanese Patent Application "kohyo" No. 11-506139

Patent Document 5: Japanese Patent Application "kohyo" No. 501869

DISCLOSURE OF THE INVENTION

Problem to be Solved by the Invention

However, the method of blowing ozone into a solution containing bromide ions to convert the bromide ions to hypobromous acid (refer to Patent Document 1) requires the provision of a large-scale, expensive ozone generator. Thus, this method suffers from the problems that a large amount of work is required for installation and production costs are high.

Further, the method of adding a hypochlorite and a bromide to a liquid to be treated, whereby the resulting reacting forms a hypobromite (refer to Patent Document 2) has a slow reaction speed, and requires 20 to 30 minutes to obtain the maximum hypobromite concentration, even if a hypochlorite is added to bromide present in the liquid to be treated to try and form the hypobromite. Since during that period the hypochlorite charged into the solution is lost by volatilization or the like, more than the required amount of hypochlorite has to be added. To avoid this, the hypochlorite and the bromide have to be mixed before adding into the liquid to be treated, which causes more work in preparation.

In the above two methods, there is also the problem that if an aqueous solution of the formed hypobromite is stored for a long period, the solution does not stabilize as hypobromous acid, but rather forms the highly toxic bromic acid ($HBrO_3$) (in Japan, the regulations on bromic acid in potable water are no greater than 0.01 mg/L). To avoid this problem, the above two methods suffer from the restriction that the production or mixing must be carried out immediately, prior to using in the liquid to be treated.

To overcome these problems, that is, increased work and costs as well as restrictions, there is the method of making a bromide present in a liquid to be treated, and then adding aqueous peracetic acid or aqueous hydrogen peroxide to form a hypobromite (refer to Patent Document 3). However, the added aqueous peracetic acid or aqueous hydrogen peroxide has a greater oxidizing power than the hypobromite, and are classified as dangerous substances under the Fire Defense Law. Thus, this method requires a considerable amount of care to be taken in handling the raw materials, and thus can hardly be recommended for practical use.

Further, to overcome the above-described problem of bromic acid formation, there is a method in which, with a sulfamate compound as a stabilizer, a hypochlorite and a bromide are pre-mixed to produce a stable hypobromite (refer to Patent Documents 4 and 5). While this method reduces the amount of bromic acid formed, the hypobromite is also stabilized if the concentration of the sulfamate in the liquid to be treated exceeds about 25 mg/L. This can consequently curtail the sterilization/anti-microbial effects of the hypobromite.

The present invention was created in view of the above-described circumstances. Particularly, the present invention is a method which can safely produce a hypobromous acid or a water-soluble salt thereof, that does hot require expensive equipment or the like, does not involve extra work such as pre-mixing or have restrictions such as producing immediately prior to use, and is simple. Further, it is an object of the present invention to provide a method which can efficiently and rapidly form a hypobromous acid or a water-soluble salt thereof which is stable and has high sterilization/anti-microbial effect, and which does not form harmful bromic acid.

Means for Solving the Problem

A first characteristic aspect of the present invention is that, in a method of forming at least either a hypobromous acid or a water-soluble salt thereof by reacting at least either a hypochlorous acid or a water-soluble salt thereof with a bromide in a liquid to be treated, at least either hypobromous acid or water-soluble salt thereof is formed by adding a modified chlorite to the liquid to be treated. While in the first characteristic aspect a hypochlorous acid (or a water-soluble salt thereof), a bromide, and a modified chlorite are added together, the order in which these are added is hot limited.

[Function and Effect]

When the at least either a hypochlorous acid or a water-soluble salt thereof (hereinafter referred to as "hypochlorite") is added to a bromide in a liquid to be treated, the bromide releases bromide ions in the liquid to be treated, which react with the hypochlorite to form a hypobromous acid or a water-soluble salt thereof (hereinafter referred to as "hypobromite").

If a chlorine-based disinfectant is used in a liquid to be treated haying a high pH, its sterilization/anti-microbial effect is reduced as a result of dissociation of the hypochlorite. On the other hand, in the case of a hypobromite, since its dissociation occurs in a pH region that is higher than that for hypochlorite, the hypobromite has a high sterilization/antimicrobial effect even in liquid to be treated having such a high pH.

In addition, the formation rate of hypobromite is faster the stronger the concentrations of the released bromide ions and hypochlorite are, and slower the weaker the concentrations are.

Usually, to directly form in Water a hypobromite having a weak hypobromous acid concentration of 1 mg/L takes 20 to 30 minutes. However, if a modified hypochlorite is added to the liquid to be treated, as a result of the action of reactive oxygen formed in the reaction [Formula 1] with the hypochlorite, chlorine dioxide having a strong sterilization power (approximately 2.6 times the sterilization effect of chlorine) and oxidizing power (approximately 10 times the oxidizing power of chlorine) across a broad pH range is formed in the liquid to be treated. The oxidizing power of this chlorine dioxide functions as a catalyst according to the reaction shown in [Formula 2], whereby as a result, a hypobromite can be formed within 2 to 10 minutes.

$$Cl_2 + Cl_4O_{10}^{2-} \rightarrow 4ClO_2 + 2Cl^- + O_2 \quad \text{[Formula 1]}$$

$$Cl_2 + 2Br^- \rightarrow Br_2 + 2Cl^- \quad \text{[Formula 2]}$$

Thus, the reaction proceeds 2 to 15 times faster than that conventionally. Accordingly, there is no need to spend time on pre-mixing the hypochlorite and the bromide and then adding to the liquid to be treated in order to increase the reaction rate. Further, since the amount of loss from volatilization as times passes after the hypochlorite was added can be decreased, the hypobromite can be formed efficiently and rapidly.

Additionally, in the present invention, since it is sufficient just to add a bromide, a hypochlorite and a modified chlorite to the liquid to be treated, large-sale and expensive equipment or dangerous reagents requiring care in handling are not used. Therefore, a hypobromite can be produced simply and safely.

Further, although the formed hypobromite is "momentarily" consumed by its action on the bacteria or microorganisms in the liquid to be treated, as shown in [Formula 3], bromide ions are produced back by the hydroxide ions in the liquid to be treated, which can be re-utilized in the formation of hypobromite, as shown in [Formula 2].

$$2Br_2 + 4OH^- \rightarrow O_2 + 4Br^- + 2H_2O \quad \text{[Formula 3]}$$

It is thus possible to recycle the bromide, which consequently means that the amount of bromide used in the liquid to be treated can be reduced, thus leading to cost reductions.

As illustrated in the below-described Examples, the facts that the hypobromite formed in accordance with the present invention: is stable without harmful bromic add being formed; has a large sterilization/anti-microbial effect; has excellent permeability even into slime; and can efficiently suppress and remove persistent slime having a high total residual halogen content, were for the first time discovered by the present inventors.

A second characteristic aspect of the present invention is that the modified chlorite is produced by mixing a peroxy compound into a sulfate-ion-containing aqueous solution having a pH of 3 or less to a level of 0.001 mol/L to 0.01 mol/L, and then mixing therein an aqueous chlorite solution into the solution so that the resulting solution has a pH of 7 or higher.

[Function and Effect]

According to this production method, a stable modified chlorite can be simply produced.

A third characteristic aspect of the present invention is that the above-described modified chlorite is tetrachlorodecaoxide.

[Function and Effect]

Tetrachlorodecaoxide (hereinafter "TCDO") is commercially available, is not subject to the legal regulations regarding the handling of dangerous substances, and can be easily obtained by anybody.

A fourth characteristic aspect of the present invention is that the molar ratio of the bromide to the modified chlorite is 1:0.002 to 0.3.

[Function and Effect]

By setting the molar ratio of the bromide to modified chlorite to 1:0.002 to 0.3, the reaction rate increases and the loss of added hypochlorite can be decreased. Therefore, the hypobromite can be formed more efficiently.

A fifth characteristic aspect of the present invention is that the bromide and the modified chlorite are added as a mixed solution of the bromide and the modified chlorite pre-mixed in water.

[Function and Effect]

As illustrated in the below-described Examples, the bromide and modified chlorite do not react with each other in water, and thus a mixed solution thereof is stable and can be stored for long periods. As a result, the management of chemical solutions can be simplified. Further, the charging operation can also be simplified, and the number of charging devices can be decreased, thus allowing a reduction in equipment costs. In addition, since the mixing ratio during charging into the liquid to be treated can be kept at a fixed level, it is possible to ensure the reproducibility of the treatment results.

A sixth characteristic aspect of the present invention is that the liquid to be treated is selected from the group consisting of process water of a pulp and paper mill, industrial circulating cooling water, and hot spring water.

[Function and Effect]

It is well known that, in a pulp mill or a paper mill, the propagation of microorganisms in the water used in the processes at the mill cause various problems. For example, the white water in a papermaking machine at a paper mill contains a large amount of pulp, which acts as a nutrient source, and is also at a suitable temperature. These points make the white water an ideal environment for the propagation of microorganisms. If microorganisms in the white water propagate, microorganisms or the metabolites thereof dump together and form a viscous substance, or what is known as "slime". If this peels away from the flow of water in the process and becomes mixed in the paper raw material, blemishes, spots, splotches and the like are formed which degrade the quality of the product. This slime can also heavily impact on operation by causing process problems such as paper tear, clogging of wire or hair, corrosion, foul odors and the like.

Methods of making paper include acidic papermaking wherein paper is made under pH conditions of 4 to 6 and neutral-alkaline papermaking wherein paper is made under pH conditions of 6 to 8. Recently, neutral-alkaline papermaking is becoming mainstream because this method does not corrode the machinery much and provides excellent paper quality. In neutral-alkaline papermaking, the pH of the water is more suitable for the proliferation and growth of microorganisms than that in conventional acidic papermaking. Further, recently the recycling of white water has been increasing, whereby the nutrient content in the water is becoming more concentrated, which, added to the increase in water temperature, makes an ideal environment for microorganisms to thrive.

However, although the slime control agents which have conventionally been used were effective in acidic pH conditions of 4 to 6, in neutral-alkaline conditions having a pH of 6 to 8 they fail to exhibit sufficient slime control effects, and thus the added amount has to be increased.

Further, in open-circulating cooling water, a high-concentration operation which recycles water is carried out in order to decrease the amount of used and waste water. In a high-concentration operation, dissolved matter in the water is concentrated, which tends to worsen water quality such as by increasing the pH for example. This can lead to the spread of disease-causing germs from Legionella bacterium, or increase problems caused by slime.

Microorganisms in an aqueous system are more likely to adhere to machinery surfaces than those floating on the surface of the water. Most of such adhered microorganisms form microcolonies which are encapsulated in an extracellular polymer consisting of polysaccharides. Foreign matter in the water interacts in a complex manner to form slime. Slime in an open-circulating cooling water system or the like not only causes waterway blockages and heat transfer problems in the heat exchanger, but the microorganisms also become a factor in corrosion. Thus, there is a strong need for countermeasures.

For slime control in a circulating aqueous system, chlorine-based biocides, such as chlorine, sodium hypochlorite, calcium hypochlorite, and chlorinated isocyanuric acid, have been used widely. It is thought that these chlorine-based slime control agents generate hypochlorous acid upon dissolution in water, which exhibits a sterilization/anti-microbial effect. However, if pH becomes high, there is the drawback that the hypochlorous acid dissociates to hypochlorous acid ions, whereby the anti-microbial effect decreases. Recently, in circulating cooling water systems, the pH often increases to around 9 as a result of high-concentration operation. In such a high pH aqueous system, chlorine-based slime control agents do not exhibit sufficient effect, whereby slime problems cannot be sufficiently controlled.

Furthermore, hot spring water from highly alkaline springs in some cases has a pH of 8.5 or even 9 or more. The sterilization or antiseptic effects from a chlorine-based disinfectant in such water cannot be expected to be particularly effective.

However, according to the present invention, since dissociation of hypobromous acid occurs at a higher pH than that for hypochlorous acid, there is the advantage that it is difficult for the sterilization/anti-microbial effect, or for the growth inhibitory effect, to be reduced even at a high pH. Therefore, the above-described slime problems or problems with sterilization/antiseptic effects in a liquid to be treated having a high pH, such as in process water (white water) of a pulp and paper mill, industrial circulating cooling water, and hot spring water, can be prevented before they occur.

BEST MODE FOR CARRYOUT THE INVENTION

Hypochlorites dissolve in water to form hypochlorous acid and hypochlorous acid ions. Specific examples of hypochlorites include hypochlorous acid, sodium hypochlorite, potassium hypochlorite, calcium hypochlorite, chlorinated isocyanuric acid and chlorine. Further, hypochlorites may also be formed by electrolysis of water containing chlorine ions.

Specific examples of bromides which release bromide ions in water (hereafter referred to as a "bromide") include hydrobromic acid, sodium bromide, potassium bromide, lithium bromide, zinc bromide and the like. Sodium bromide is preferred as the bromide.

Specific examples of the modified chlorite which can be used include those described in Japanese Patent Application "kokoku" No. 6-102522. In the present embodiment, tetrachlorodecaoxide (hereinafter "TCDO") is used.

Examples of the formation method are illustrated in the following (1) to (3).

(1) Separately add a bromide and TCDO to an aqueous system of interest, and then add a hypochlorite to this solution.

(2) First, prepare a formulation with a bromide and TCDO mixed in a single solution, add the formulation to the aqueous system and then add the hypochlorite.

(3) First, prepare a formulation consisting of, mixed in a single solution, a dispersant used for scale prevention or the like, a chemical used for a purpose other than sterilization/anti-microbial effect, such as an anti-corrosion agent used for preventing corrosion of iron or copper pipes, a bromide and TCDO, add the formulation to the aqueous system and then add the hypochlorite.

The most preferable embodiment among these is, as illustrated as the above-described methods (2) and (3), to first prepare a formulation with a bromide and TCDO mixed in a single solution, add the formulation to the aqueous system and then add the hypochlorite. This method has the advantages that, since the bromide and TCDO do not react with each other in water, the resulting solution can be stably stored for long periods, and that charging management is simplified; for example, the mixing ratio during charging into the aqueous system can be kept at a fixed level, and the number of charging devices can be decreased. As illustrated as the above method (3), the number of charging devices can be further decreased in the case of using a stable combination consisting of a dispersant used for scale prevention or the like, a chemical used for a purpose other than sterilization/anti-microbial effect, such as an anti-corrosion agent used for preventing corrosion of the iron or copper pipes, a bromide and TCDO. The advantages of this are substantial.

The reaction between the hypochlorite and TCDO progresses more rapidly than the reaction between the hypochlorite and bromide. Therefore, the hypochlorite preferentially reacts with TCDO, and the remaining hypochlorite reacts with the bromide.

TABLE 1

Relative volatility of the sterilant/anti-microbial agent

| Sterilant/anti-microbial agent | Relative volatility |
|---|---|
| Hypobromous acid | 1 |
| Hypochlorous acid | 2 |
| Chlorine dioxide | 1,800 |
| Ozone | 200,000 |

As shown in Table 1, the formed chlorine dioxide is highly volatile. It is thus considered that the chlorine dioxide volatizes without participating in the formation of the hypochlorite. It is sufficient for the chlorine dioxide to be a catalytic factor. The bromide and TCDO molar ratio at this point is preferably 1:(0.002 to 0.3), and more preferably, 1:(0.01 to 0.1). If the TCDO is less than 0.002 times (molar ratio), the formation rate of the hypobromite is slowed. If the TCDO is more than 0.3 times (molar ratio), the formation of the hypobromite is sufficient, although excessively formed chlorine dioxide is volatized, thereby increasing the loss of the added hypochlorite, which is economically disadvantageous.

The molar ratio of the bromide in the aqueous system and the added hypochlorite should be such that 0.4 to 0.8 times of hypochlorite is added based on the bromide, and preferably, 0.5 to 0.7 times. If less than 0.4 times (molar ratio) of hypochlorite based on the bromide, the added bromide is wasted. If more than 0.8 times (molar ratio) of hypochlorite based on the bromide, the hypobromite is volatizes. This is not preferable, since the decreasing bromide ions cannot be sufficiently replenished, which causes a bromide deficiency.

In whichever case, if the total mole number of bromide and TCDO is less than the mole number of the hypochlorite, hypochlorite will remain. However, the remaining hypochlorite itself has a slime control function, and thus poses no hindrance whatsoever on the advantageous effects of the present invention being expressed.

The hypochlorite, bromide and TCDO are all soluble in water, and thus each of these components can be added as a solid into the aqueous system of interest. Alternatively, an aqueous solution for each of these can be prepared, and such solutions added into the aqueous system of interest. However, when they are added into the aqueous system in solid form, the time required to dissolve differs for each component, while even in addition of the aqueous solutions into the aqueous system, the time required depends on their behavior of diffusion in the water. Therefore, the progress of the reaction when adding each of the hypochlorite, the bromide and TCDO components either simultaneously or close thereto, will obviously depend on the dissolution rates or dispersion states.

In the case of pre-mixing the TCDO and bromide in water, the pH of the water in which these are mixed is 9 to 12, and preferably, 10 to 11. If the pH is less than 9, TCDO decomposes into chlorine gas and bromine gas, which are easily volatized. If the pH exceeds 12, this can raise the pH of the liquid to be treated to 9 or more. This is not preferable, as the conversion rate to the hypobromite in the liquid to be treated decreases.

The pH of the liquid to be treated which is used by the method according to the present invention is preferably 5 to 10, and more preferably, 6 to 9.5. If the pH of the liquid to be treated exceeds 9.5, hypobromite cannot be efficiently formed in the reaction between the hypochlorite and bromide in spite of the addition of TCDO, and thus slime control effects deteriorate. Further, if the pH is 5 or less, the causes, of corrosion may be aided by the oxidizer, which is not preferable.

In a preferable embodiment according to the present invention, the amount of hypochlorite, bromide and TCDO added to the aqueous system to be treated cannot be uniformly determined, as this will depend on the compositional ratio of these slime control agent compositions, the water quality of the aqueous system to be treated, the amount of slime, the addition frequency and the like. Usually, based on the water of the aqueous system, it is preferable for 0.1 to 50 ppm, and preferably, 0.2 to 20 ppm, and more preferably, 0.5 to 10 ppm, of hypobromous acid (calculating the hypobromite as hypobromous acid) to be formed.

If the formed amount of hypobromous acid (calculating the hypobromite as hypobromous acid) is less than 0.1 ppm, essentially, manifestation of the hypobromous acid effects cannot be expected. Further, if the formed amount of hypobromous acid (calculating the hypobromite as hypobromous acid) is more than 50 ppm, while the effects are sufficient, no additional improvement in effects is seen, yet such amount is uneconomic, and from the viewpoint of environmental pollution, is not preferable.

The method of adding the hypochlorite, bromide and TCDO to the aqueous system of interest is not especially limited, and is usually performed, for example, using a metering pump.

The residual concentration of hypobromous acid can be measured by a well-known method, such as diethyl-p-phenylenediammonium (DPD) colorimetry, DPD-ammonium iron(II) sulfate titration [JIS K 0101], and SBT testing (Dojindo Laboratories).

In these testing methods, the free residual halogen content, the combined content of free residual bromine and chlorine dioxide, and the total residual halogen content in the water are determined. Here, the free residual halogen content is the sum of the free residual chlorine content, the free residual bromine content and the chlorine dioxide content; and the total residual halogen content is the sum of the free residual halogen content and the bound residual halogen content. The free residual bromine content here refers to the total of the hypobromous acid and hypobromous acid ions.

For the DPD colorimetry and DPD-ammonium iron(II) sulfate titration, simple analysis kits are commercially available from Hach Company and LaMotte Chemical Products. For the SBT testing, a residual chlorine measuring kit-SBT test is commercially available from Dojindo Laboratories. These can be used for managing the residual concentration in the method according to the present invention.

Further, the residual concentration of hypobromous acid from oxidation-reduction can be determined by utilizing the influence that the residual concentration of, the hypobromite has oh redox potential to separately determine the correlation between concentration and redox potential. This method is convenient in practice.

The hypobromite formed in the present invention can be applied to, for example, process water from pulp mill or paper mill processes, an open-circulating aqueous system, hot spring water, and liquid to be treated from various other aqueous systems (e.g. process water from various industries, industrial aqueous systems of cooling water, washing water, waste water or the like, water storage tanks, swimming pools, hot spring water, ornamental ponds and the like).

Process water from a pulp or paper can include water collectively designated "white water", such as that from a grind process, a papermaking process, a screen process, and a bleaching process, as well as any water which is handled in other processes at a pulp mill or paper mill. It was confirmed that even if hypobromite formed according to the present invention is added in the above-described concentration, there is no affect on the processes, and further, that product quality is not harmed.

When the present method is applied to an open-circulating aqueous system, blockages in the heat exchanger or pipes from slime formation, and deterioration in heat conduction can be suppressed. The slime control method according to the present invention is effective against iron bacteria, which is a kind of aerobic bacteria. The slime control method according to the present invention also has good slime permeability and excellent slime removing effect, so that applying the present method has as effect even on sulfate-reducing bacteria which are susceptible to forming in the anaerobic atmosphere beneath slime, thus allowing the prevention of corrosion induced by iron bacteria or sulfate-reducing bacteria.

In the aqueous system, in addition to slime control, a pitch control agent, a defoaming agent and the like may be simultaneously used in the process water from a pulp mill or a paper mill. In ah open-circulating aqueous system, a corrosion inhibitor, such as a zinc salt, polyphosphate, organic phosphonic acid, an azole compound, molybdate and the like; a scale inhibitor using a polymer which contains acrylic acid, maleic acid or the like; and a dispersant using various surfactants may be used simultaneously. The present invention does not bar mixing or concomitant use with these various formulations within the range in which the effectiveness of the present invention is not harmed.

EXAMPLES

The present invention will now be specifically described. However, the present invention is not limited to the following examples.

[Analysis of Free Residual Chlorine, Free Residual Bromine and Chlorine Dioxide, and Total Residual Halogen]

Measurement of the free residual chlorine, the combined content of free residual bromine and chlorine dioxide, and the bound residual halogen concentrations in a water sample were carried out using the following "residual chlorine measuring kit-SBT test" which is commercially available from Dojindo Laboratories.

(1) Analytical method:

i. Measurement of Free Residual Halogen Content

As specified by the "residual chlorine measurement kit-SBT test", 0.2 ml of a test water adjustment solution was added to 10 ml of test water, and 0.1 ml of pigment solution was then added to the resulting solution. The obtained color was measured as chlorine concentration [$mgCl_2/L$] using the colorimeter attached to the kit.

ii. Measurement of the Combined Content of Free Residual Bromine and Chlorine Dioxide 0.5 ml of a 10% glycerin solution was charged into 10 ml of test water, and 0.2 ml of a test water adjustment solution was rapidly added to this solution. Then, 0.1 ml of pigment solution was added to the resulting solution. The obtained color was measured as chlorine concentration [$mgCl_2/L$] using the colorimeter attached to the kit.

iii. Measurement of Total Residual Halogen Content

As specified by the "residual chlorine measurement kit-SBT test", 0.2 ml of a test water adjustment solution was added to 10 ml of test water. Next, 0.1 ml of pigment solution was added to the resulting solution, and then 0.15 ml of a 5% potassium iodide solution was added thereto. The obtained color was measured as chlorine concentration [$mgCl_2/L$] using the colorimeter attached to the kit.

(2) Here, the free residual chlorine, the combined content of free residual bromine and chlorine dioxide, and the combined residual halogen are all expressed in terms of chlorine ($Cl_2$). The free residual halogen content and the total residual halogen content are as illustrated in the following [Expression 1].

Concerning the "residual chlorine measurement kit-SBT test" used in the present invention, the linearity of this kit is not only for chlorine but for bromine guaranteed in the measurements. However, because bromine has low specificity, it is difficult to individually measure only bromine. Accordingly, for convenience, by introducing the concept of the combined content of free residual bromine and chlorine dioxide, and measuring their concentrations together as chlorine concentration [$mgCl_2/L$], the formation/decomposition of bromine can be indirectly evaluated.

Free residual halogen content=(free residual chlorine content)+(free residual bromine content)+(chlorine dioxide content)

Total halogen content=(free residual halogen content)+(combined residual halogen content)  [Expression 1]

Example 1

A test solution having a total volume of 1 L was prepared by dissolving 1.8 g of weighed-out disodium hydrogen phosphate $Na_2HPO_4$ in 500 ml of pure water, and then mixing into this solution 0.05 g of sodium dihydrogen phosphate dihydrate $Na_2H_2PO_4 \cdot 2H_2O$ and dissolving. The pH of the resulting solution was 8.50. The solution was sampled in 100 ml beakers, and then charged with 0.04 mmol/L (4.1 mg/L) of sodium bromide and TCDO ("Hydroxan", containing 20% TCDO active constituent, manufactured by Tohzai Chemical Industry Co., Ltd.). The added amount of TCDO varied between 0.0000 mmol/L to 0.0200 mmol/L. Finally, a sodium hypochlorite solution was added in an amount so that the free residual chlorine concentration [$mgCl_2/L$] was 2 $mgCl_2/L$. The free residual halogen content [$mgCl_2/L$] and the combined content of free residual bromine and chlorine dioxide [$mgCl_2/L$] were both measured over time after addition.

The maximum chlorine dioxide content that is obtainable from the added 0.0026 mmol/L of TCDO is 0.38 $mgCl_2/L$ as chlorine concentration [$mgCl_2/L$].

$$Cl_2+Cl_4O_{10}^{2-} \rightarrow 4ClO_2+2Cl^- \quad \text{[Formula 4]}$$

| Molecular weights: | 71 | 302 | 142 (as $Cl_2$) |
|---|---|---|---|
| mg/L: | 0.19 | 0.8 | 0.38 (as $Cl_2$) |

The maximum amount of hypobromous acid that is obtainable from the added 0.04 mmol/L of sodium bromide is 1.4 $mgCl_2/L$ as chlorine concentration [$mgCl_2/L$].

$$Cl_2+2NaBr \rightarrow Br_2+2NaCl \quad \text{[Formula 5]}$$

| Molecular weights: | 71 | 206 | 71 (as $Cl_2$) |
|---|---|---|---|
| mg/L: | | 4.1 | 1.4 (as $Cl_2$) |

The added amounts and measurement results are shown in Table 2 and FIGS. 1 and 2.

TABLE 2

| Test sample | TCDO mmol/L | NaBr/ mmol/L | $Cl_2$ mg/L | Time/min | 5 | 10 | 30 | 60 | 120 |
|---|---|---|---|---|---|---|---|---|---|
| A | 0.00265 | 0 | 2 | Free residual halogen content ($mgCl_2/L$) | 1.5 | 1.4 | 1.3 | 1.25 | 1.2 |
| | | | | Combined content | 0.05 | 0.05 | 0.05 | 0.05 | 0.05 |

TABLE 2-continued

| Test sample | TCDO mmol/L | NaBr mmol/L | Cl$_2$ mg/L | Time/min | 5 | 10 | 30 | 60 | 120 |
|---|---|---|---|---|---|---|---|---|---|
| B | 0.00000 | 0.04 | 2 | Free residual halogen content (mgCl$_2$/L) | 1.5 | 1.4 | 1.35 | 1.3 | 1.25 |
| | | | | Combined content of free residual bromine and chlorine dioxide (mgCl$_2$/L) | 1.2 | 1.25 | 1.3 | 1.25 | 1.2 |
| C | 0.00007 | 0.04 | 2 | Free residual halogen content (mgCl$_2$/L) | 1.4 | 1.45 | 1.5 | 1.4 | 1.3 |
| | | | | Combined content of free residual bromine and chlorine dioxide (mgCl$_2$/L) | 1.3 | 1.35 | 1.4 | 1.35 | 1.25 |
| D | 0.00033 | 0.04 | 2 | Free residual halogen content (mgCl$_2$/L) | 1.3 | 1.45 | 1.5 | 1.35 | 1.25 |
| | | | | Combined content of free residual bromine and chlorine dioxide (mgCl$_2$/L) | 1.1 | 1.3 | 1.45 | 1.35 | 1.25 |
| E | 0.00066 | 0.04 | 2 | Free residual halogen content (mgCl$_2$/L) | 1.3 | 1.4 | 1.5 | 1.45 | 1.3 |
| | | | | Combined content of free residual bromine and chlorine dioxide (mgCl$_2$/L) | 1.3 | 1.4 | 1.5 | 1.45 | 1.3 |
| F | 0.00199 | 0.04 | 2 | Free residual halogen content (mgCl$_2$/L) | 1.3 | 1.5 | 1.55 | 1.5 | 1.4 |
| | | | | Combined content of free residual bromine and chlorine dioxide (mgCl$_2$/L) | 1.2 | 1.5 | 1.55 | 1.5 | 1.4 |
| G | 0.00331 | 0.04 | 2 | Free residual halogen content (mgCl$_2$/L) | 1.4 | 1.55 | 1.6 | 1.55 | 1.45 |
| | | | | Combined content of free residual bromine and chlorine dioxide (mgCl$_2$/L) | 1.4 | 1.55 | 1.6 | 1.55 | 1.45 |
| H | 0.00662 | 0.04 | 2 | Free residual halogen content (mgCl$_2$/L) | 1.5 | 1.6 | 1.7 | 1.5 | 1.3 |
| | | | | Combined content of free residual bromine and chlorine dioxide (mgCl$_2$/L) | 1.5 | 1.6 | 1.6 | 1.5 | 1.3 |
| I | 0.01325 | 0.04 | 2 | Free residual halogen content (mgCl$_2$/L) | 1.6 | 1.6 | 1.7 | 1.5 | 1.3 |
| | | | | Combined content of free residual bromine and chlorine dioxide (mgCl$_2$/L) | 1.6 | 1.6 | 1.6 | 1.5 | 1.3 |
| J | 0.01987 | 0.04 | 2 | Free residual halogen content (mgCl$_2$/L) | 1.7 | 1.5 | 1.3 | 1.2 | 1.15 |
| | | | | Combined content of free residual bromine and chlorine dioxide (mgCl$_2$/L) | 1.7 | 1.5 | 1.3 | 1.2 | 1.15 |

TABLE 2-continued

| Test sample | TCDO mmol/L | NaBr/ mmol/L | Cl$_2$ mg/L | Time/min | 5 | 10 | 30 | 60 | 120 |
|---|---|---|---|---|---|---|---|---|---|
| K | 0.00265 | 0.04 | 0 | Free residual halogen content (mgCl$_2$/L) | 0.0 | 0.0 | 0.0 | 0.0 | 0.0 |
|  |  |  |  | Combined content of free residual bromine and chlorine dioxide (mgCl$_2$/L) | 0.0 | 0.0 | 0.0 | 0.0 | 0.0 |

In the case of adding sodium hypochlorite to TCDO, the chlorine dioxide is eliminated as soon as it is formed. The chlorine dioxide that could be confirmed was only 0.05 mgCl$_2$/L. In the case of adding sodium hypochlorite to sodium bromide, the maximum peak occurs 30 minutes after addition. The maximum value at this point was 1.3 mgCl$_2$/L, which is under 1.4 mgCl$_2$/L. If TCDO is added to a combination of a bromide and a hypochlorous acid, the maximum peak value increases as the amount of added TCDO increases, whereby it is clear that the time taken to arrive the maximum peak value is faster and that the hypobromous acid is being formed rapidly. These results showed that if the bromide and TCDO molar ratio exceeds 1:0.5, the added hypochlorous acid is consumed by chlorine dioxide formation and is volatized at a high speed.

Example 2

Neutral papermaking process white water from a paper mill having a pH of around 7 was used as the test solution. The results of testing with the same additions as in Example 1 while varying the kind of bromide and hypochlorite are shown in Table 3.

TABLE 3

| TCDO mmol/L | Bromide mmol/L | Hypochlorite mg Cl$_2$/L | Content | 5 | 10 | 30 | 60 |
|---|---|---|---|---|---|---|---|
| 0.00000 | KBr 0.04 | NaClO 3 | Combined content of free residual bromine and chlorine dioxide (mgCl$_2$/L) | 1.2 | 1.2 | 1.3 | 1.2 |
| 0.00265 | KBr 0.04 | NaClO 3 | Combined content of free residual bromine and chlorine dioxide (mgCl$_2$/L) | 1.4 | 1.5 | 1.5 | 1.4 |
| 0.00265 | HBr 0.04 | NaClO 3 | Combined content of free residual bromine and chlorine dioxide (mgCl$_2$/L) | 1.5 | 1.5 | 1.4 | 1.4 |
| 0.00265 | LiBr 0.04 | NaClO 3 | Combined content of free residual bromine and chlorine dioxide (mgCl$_2$/L) | 1.4 | 1.5 | 1.4 | 1.4 |
| 0.00265 | ZnBr 0.04 | NaClO 3 | Combined content of free residual bromine and chlorine dioxide (mgCl$_2$/L) | 1.3 | 1.5 | 1.5 | 1.4 |
| 0.00265 | NaBr 0.04 | NaClO 3 | Combined content of free residual bromine and chlorine dioxide (mgCl$_2$/L) | 1.4 | 1.5 | 1.5 | 1.4 |
| 0.00265 | NaBr 0.04 | CaClO 3 | Combined content of free residual bromine and chlorine dioxide (mgCl$_2$/L) | 1.3 | 1.5 | 1.5 | 1.4 |
| 0.00265 | NaBr 0.04 | Sodium Dichloroisocyanurate 3 | Combined content of free residual bromine and chlorine dioxide (mgCl$_2$/L) | 1.4 | 1.5 | 1.4 | 1.4 |

Hypochlorous acid, sodium hypochlorite; potassium hypochlorite, calcium hypochlorite, chlorinated isocyanuric acid, and the like could be used as the hypochlorite. Obviously, hydrobromic acid, sodium bromide, potassium bromide, lithium bromide, zinc bromide and the like can be used as the bromide.

Example 3

BALSTER DT (sodium hypochlorite manufactured by Tohzai Chemical Industry Co., Ltd; 10% effective chlorine) sodium bromide, and Hydroxan (containing 20% TCDO, manufactured by Tohzai Chemical Industry Co., Ltd.) were charged together into open-circulating cooling water (pH 8.6) having a retained water volume of 18 m$^3$ and circulating at 60 m$^3$/hr for a comparison with the effects of the present invention. (Blowing was stopped during the testing.)

The measurement results of the free residual halogen content, the total residual halogen content and the combined content of the free residual bromine and chlorine dioxide, pH of the liquid to be treated (open-circulating cooling water) at two points in time, prior to the start of testing (prior to charging of the respective additives) and once testing had finished, and the respective BrO$_3^-$ and Br$^-$ ion concentrations determined by ion chromatography, are shown in the following respective concentration measurement results. Hyphens ("-") in the tables mean that testing could not be performed.

Comparative Example 1

Only BALSTER DT was added. The results were as follows.

TABLE 4

| Additive name | Added amount | Active constituent | Initial concentration of active constituent |
|---|---|---|---|
| BALSTER DT | 300 g | Chlorine | 1.67 ppm (as $Cl_2$) |

TABLE 5

Concentration measurement results

| | $mgCl_2/L$ | | | | | |
|---|---|---|---|---|---|---|
| | Free | Total | Combined content | | mg/L | |
| Time/min after addition | residual halogen content | residual halogen content | of free residual bromine and chlorine dioxide | pH 8.6 | $BrO_3^-$ ions 0.000 | $Br^-$ ions 0.000 |
| 5 | 0.15 | 1.04 | 0.00 | — | — | — |
| 10 | 0.15 | 0.98 | 0.00 | — | — | — |
| 20 | 0.15 | 0.60 | 0.00 | — | — | — |
| 30 | 0.05 | 0.42 | 0.00 | — | — | — |
| 40 | 0.03 | 0.32 | 0.00 | 8.5 | 0.000 | 0.000 |

In Comparative Example 1, pH was high, and the free residual halogen content was detected as only about 16% of the total residual halogen content (=total chlorine content), whereby it can be understood that the oxidation capacity is poor.

Comparative Example 2

BALSTER DT and Hydroxan were combined. The results were as follows.

TABLE 6

| Additive name | Added amount | Active constituent | Initial concentration of active constituent |
|---|---|---|---|
| BALSTER DT | 300 g | Chlorine | 1.67 ppm (as $Cl_2$) |
| Hydroxan | 120 g | TCDO | 1.33 ppm (as $ClO_2$) |

TABLE 7

Concentration measurement results

| | mg $Cl_2$/L | | | | | | |
|---|---|---|---|---|---|---|---|
| | Free | Total | Combined content of free residual bromine and | Combined content of free residual bromine and | | mg/L | |
| Time/min after addition | residual halogen content | residual halogen content | chlorine dioxide (measured in cooling tower) | chlorine dioxide 5 min after sampling | pH 8.6 | $BrO_3^-$ ions 0.000 | $Br^-$ ions 0.000 |
| 5 | 0.00 | 0.74 | 0.00 | 0.55 | 8.5 | — | — |
| 10 | 0.00 | 0.61 | 0.00 | 0.55 | 8.5 | — | — |
| 20 | 0.00 | 0.54 | 0.00 | 0.40 | 8.4 | — | — |
| 30 | 0.00 | 0.40 | 0.00 | 0.30 | 8.3 | — | — |
| 40 | 0.00 | 0.24 | 0.00 | 0.20 | 6.3 | 0.000 | 0.000 |

In Comparative Example 2, no free residual halogen was found in the pit of the cooling tower, but the level of chlorine dioxide in test water stored in a beaker assayed five minutes after sampling was given as the combined content of free residual bromine and chlorine dioxide of the water assayed five minutes after sampling shown by the concentration measurement results in Table 7. This result suggests that chlorine dioxide forms from a combination of the modified chlorous acid and the hypochlorite, but the chlorine dioxide has already volatilized and decomposed when it falls onto the water spray plate of the cooling tower. In contrast, the test water exhibits the presence chlorine dioxide definitely formed which was sampled and left to stand for 5 minutes and then assayed for chlorine dioxide. That is, while the hypochlorite has a pH of 8.5, and thus forms combined chlorine, chlorine dioxide gradually forms by the addition of the modified hypochlorous acid. However, the formed chlorine dioxide should be immediately volatilized due to agitation caused by trickling in the cooling tower. Therefore, chlorine dioxide cannot be used alone in the cooling tower.

Comparative Example 3

BALSTER DT and sodium bromide were combined. The results were as follows.

TABLE 8

| Additive name | Added amount | Active constituent | Initial concentration of active constituent |
|---|---|---|---|
| BALSTER DT | 300 g | Chlorine | 1.67 ppm (as $Cl_2$) |
| Sodium bromide | 120 g | Bromide ions | 6.67 ppm (as $Br^-$) |

TABLE 9

Concentration measurement results

| | mgCl$_2$/L | | | | mg/L | |
|---|---|---|---|---|---|---|
| Time/min after addition | Free residual halogen content | Total residual halogen content | Combined content of free residual bromine and chlorine dioxide | pH 8.4 | BrO$_3$- ions 0.000 | Br- ions 5.231 |
| 5 | 0.40 | 1.13 | 0.40 | 8.4 | — | — |
| 10 | 0.50 | 1.03 | 0.50 | 8.4 | — | — |
| 20 | 0.60 | 0.89 | 0.60 | 8.4 | — | — |
| 30 | 0.41 | 0.73 | 0.42 | 8.4 | — | — |
| 40 | 0.24 | 0.52 | 0.24 | 8.3 | — | — |
| 50 | 0.15 | 0.49 | 0.15 | 8.3 | — | — |
| 60 | 0.10 | 0.42 | 0.10 | 8.3 | 0.000 | 3.580 |

In Comparative Example 3, it was confirmed that a hypobromous add formed, which caused sterilizing oxidation to occur. However, it took 20 minutes for the hypobromous add to arrive at its maximum peak value, which shows that the reaction rate was slow.

In Comparative Example 3, the decomposition of chlorine was slower than that in Comparative Example 1, where only a hypochlorous acid was added, and the total residual halogen content could be maintained for about 20 minutes longer. For example, comparing how long it took (minutes) after charging for the total residual halogen content to decrease to 0.42 mgCl$_2$/L, while this took about 30 minutes in Comparative Example 1, it took about 60 minutes in the present example. Therefore, vaporization of hypobromous acid is obviously twice as slow as that for hypochlorous acid.

Working Example 1

BALSTER DT, sodium bromide and Hydroxan were combined. The results were as follows.

TABLE 10

| Additive name | Added amount | Active constituent | Initial concentration of active constituent |
|---|---|---|---|
| BALSTER DT | 300 g | Chlorine | 1.67 ppm (as Cl$_2$) |
| Sodium bromide | 80 g | Bromide ions | 4.44 ppm (as Br—) |
| Hydroxan | 120 g | TCDO | 1.33 ppm (as ClO$_2$) |

TABLE 11

Concentration measurement results

| | mg Cl$_2$/L | | | | mg/L | |
|---|---|---|---|---|---|---|
| Time/min after addition | Free residual halogen content | Total residual halogen content | Combined content of free residual bromine and chlorine dioxide | pH 8.4 | BrO$_3$- ions 0.000 | Br- ions 2.785 |
| 5 | 0.60 | 1.20 | 0.60 | 8.4 | — | — |
| 10 | 0.46 | 0.80 | 0.45 | 8.4 | — | — |
| 20 | 0.34 | 0.55 | 0.30 | 8.4 | — | — |
| 30 | 0.20 | 0.35 | 0.20 | 8.4 | — | — |
| 40 | 0.13 | 0.22 | 0.13 | 8.3 | — | — |
| 50 | 0.05 | 0.20 | 0.05 | 8.3 | 0.000 | 2.318 |

In Working example 1, a hypobromous acid was formed by a very vigorous reaction, which caused a sterilizing oxidation to occur. The hypobromous acid did not even take 5 minutes to reach its maximum peak, thus showing the effects of stirring in the cooling tower on further hastening the formation rate.

Although the decomposition of chlorine was not as slow in Working example 1 as that for only a hypobromous acid, it was not as fast as that for chlorine dioxide. The decomposition was about the same as that for a hypochlorous add.

Working Example 2

The residual sodium bromide from Working example 1 was further charged with Hydroxan and BALSTER DT. The results were as follows.

TABLE 12

| Additive name | Added amount | Active constituent | Initial concentration of active constituent |
|---|---|---|---|
| BALSTER DT | 300 g | Chlorine | 1.67 ppm (as Cl$_2$) |
| Sodium bromide | 0 g | Bromide ions | 0 ppm (as Br—) |
| Hydroxan | 120 g | TCDO | 1.33 ppm (as ClO$_2$) |

TABLE 13

Concentration measurement results

| | mg Cl$_2$/L | | | | mg/L | |
|---|---|---|---|---|---|---|
| Time/min after addition | Free residual halogen content | Total residual halogen content | Combined content of free residual bromine and chlorine dioxide | pH 8.4 | BrO$_3$- ions 0.000 | Br- ions 2.318 |
| 5 | 0.55 | 1.08 | 0.55 | 8.4 | — | — |
| 10 | 0.35 | 0.89 | 0.35 | 8.4 | — | — |
| 20 | 0.25 | 0.67 | 0.25 | 8.4 | — | — |
| 30 | 0.22 | 0.51 | 0.22 | 8.4 | — | — |
| 40 | 0.19 | 0.41 | 0.19 | 8.4 | — | — |
| 50 | 0.12 | 0.36 | 0.12 | 8.4 | 0.000 | 1.918 |

In Working example 2, the hypobromous acid also rapidly formed from the residual bromide ions. There was no change in the sterilizing oxidation occurring.

The change in bromide ions between Comparative Example 3, and Working examples 1 and 2 will now be compared. In Comparative Example 3, about 1.65 ppm (as Br$^-$) of bromide ions were lost in the situation where 0.6 ppm (as Cl$_2$) of hypobromous acid was detected. *However, if TCDO is added, only* 0.467 ppm (as Br) of bromide ions were lost (Examples 1 and 2 had the same result). In other words, it was confirmed that the bromide which has turned into hypobromous acid changed back into bromide ions if an oxidant was used.

Accordingly, it was proven that reuse of the bromide ions is possible by the addition of a modified chlorite solution.

Further, bromic add did not form even when a modified chlorite solution was added, so that there is absolutely no concern about the formation of bromic acid.

Example 4

Sodium hypochlorite was charged into bath water which used pH 9.2 hot spring water so that the free residual chlorine concentration would be detected as 0.5 mg/L. Legionella bacteria were detected in the bath water at a level of 1,000 cfu/100 ml. In the alkaline region, even among free residual chlorine, hypochlorous acid ions which have a weak sterilization power become the main component, thereby showing that the sterilization effect is attenuated.

Thus, while adding a sodium hypochlorite solution which would be detected at 0.5 mgCl$_2$/L as free residual chlorine, sodium bromide was added to a level of 1 mg/L. As a result, the free residual bromine concentration in the bath water was detected as 0.25 mgCl$_2$/L. The legionella bacteria in the bath water were detected at a level of 100 cfu/100 ml, which means that the sterilization effect against legionella bacteria in the bath water had strengthened from the formation of hypobromous acid having a sterilization effect in the alkaline region. In addition, while adding a sodium hypochlorite solution which would be detected as 0.5 mgCl$_2$/L as free residual chlorine, sodium bromide was added to a level of 1 mg/L, and Hydroxan (20% TCDO, manufactured by Tohzai Chemical Industry Co., Ltd.) was added to a level of 0.7 mg/L. As a result, the number of legionella bacteria in the bath water was no more than 10 cfu/100 ml, which was at or blow the detection limit. At that point, die free residual bromine concentration in the bath water was detected as 0.4 mgCl$_2$/L. This can be thought of as being the result of adding TCDO into the bath water, whereby the TCDO reacted with free residual chlorine to form chlorine dioxide, thereby further promoting the formation of hypobromous acid from the reaction of the bromide ions in the bath water.

By using TCDO and bromide ions together with sodium hypochlorite, the sterilization effect of bath water using alkaline hot spring water, which has been said to be difficult to sterilize with conventional hypochlorous acid or the like, was able to be improved.

Example 5

A formulation was prepared consisting of 4% polymaleic acid (scale preventing agent), 1% benzotriazole (anti-corrosion agent for copper), 3% sodium hydroxide (stabilizer), 2% sodium bromide and 3% Hydroxan.

This formulation had a pH which was adjusted to 10 or higher, and was stable for three months or longer at 5° C., room temperature, or even 50° C. This formulation was added to an open-circulating cooling water system (pH of 8.4) operating at a seven-times concentration, and controlled so that the concentration in the circulating water was maintained at 200 mg/L. This open-circulating cooling water system was operated 24 hours a day. 1 mgCl$_2$/L of free residual chlorine based on the retained water volume was added 10 times per day, every hour from 8 a.m. to 5 p.m. For a sodium hypochlorite solution having a 10% effective chlorine, 100 (mg)/retained water volume (L) per day was added. The states of the cooling water after addition at 10 a.m. and on addition at 5 p.m. were as follows.

TABLE 14

| | Adding at 10 a.m. | | | | Adding at 5 p.m. | | | |
| | mg Cl$_2$/L | | | | mg Cl$_2$/L | | | |
| Time/min after addition | Free residual halogen content | Total residual halogen content | Combined content of free residual bromine and chlorine dioxide | mg/L Br- ions | Free residual halogen content | Total residual halogen content | Combined content of free residual bromine and chlorine dioxide | mg/L Br- ions |
| --- | --- | --- | --- | --- | --- | --- | --- | --- |
| 5  | 0.33 | 0.50 | 0.28 | 1.081 | 0.23 | 0.55 | 0.15 | 0.503 |
| 10 | 0.29 | 0.35 | 0.27 | —     | 0.22 | 0.44 | 0.15 | —     |
| 20 | 0.29 | 0.20 | 0.26 | —     | 0.21 | 0.30 | 0.13 | —     |
| 30 | 0.20 | 0.13 | 0.15 | —     | 0.15 | 0.20 | 0.12 | —     |
| 40 | 0.13 | 0.07 | 0.10 | 0.945 | 0.10 | 0.13 | 0.08 | 0.352 |

Hypobromous acid formed rapidly during the hypochlorous acid addition, and sterilization/anti-microbial effects were also evident at the concentration in the system. No signs of slime problems were seen in the cooling tower or even the heat exchanger copper tubing during operation for a three month period over, summer from July to September. This system was maintained using two pumps, a conventional chemical injection pump for an anti-corrosion dispersant and a disinfectant pump for sodium hypochlorite. Switching to a stable formulation by adding sodium bromide and TCDO to the anti-corrosion dispersant allowed the sterilization/anti-microbial effects to be easily improved.

From the above test results, as described in the present invention, it was confirmed that the method of forming at least either a hypobromous acid or a water-soluble salt thereof in the liquid to be treated by making a bromide which releases bromide ions and a modified chlorite present in a liquid to be treated, and then adding at least either a hypochlorous acid or water-soluble salt thereof, is excellent.

INDUSTRIAL UTILITY

Since the propagation of microorganisms in water having a high pH can be suppressed, the present invention can be applied to applications such as sterilization or disinfection of the water used in a pulp mill or a paper mill, open-circulating cooling water, hot spring water or the like, or for prevention of slime problems or the like.

Figure 1:
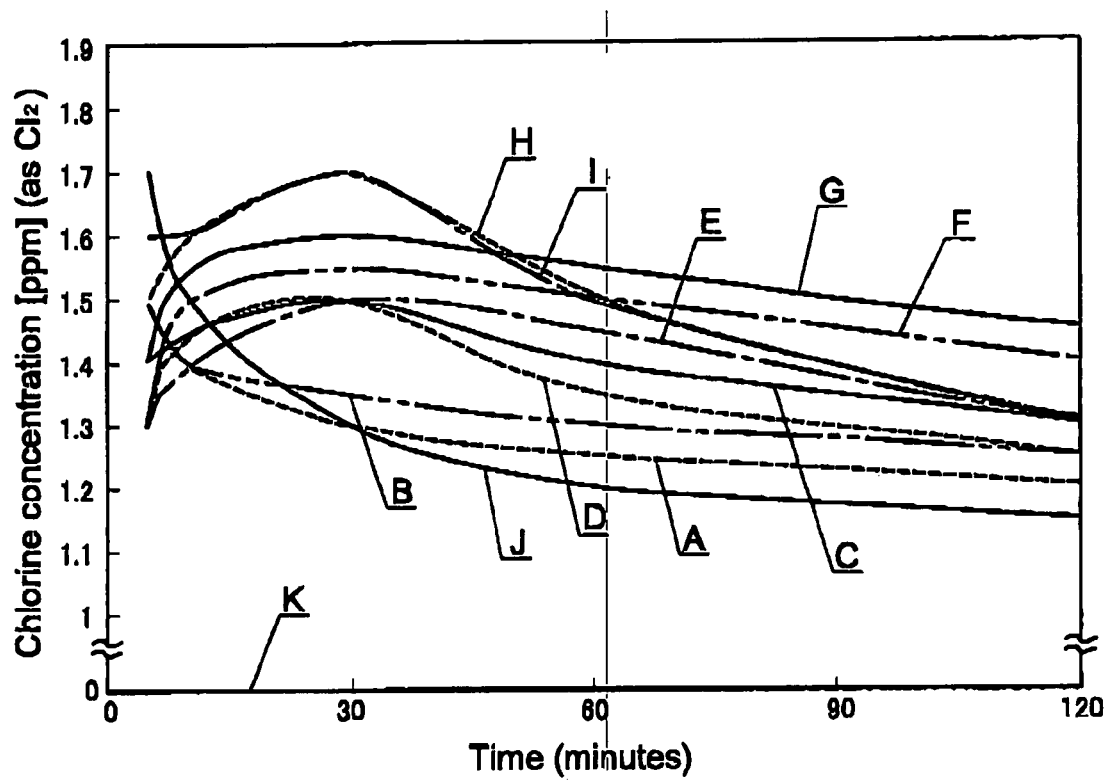
FIG. 1 is a graph showing the change over time in the free residual halogen content for each of the tests.
Figure 2:
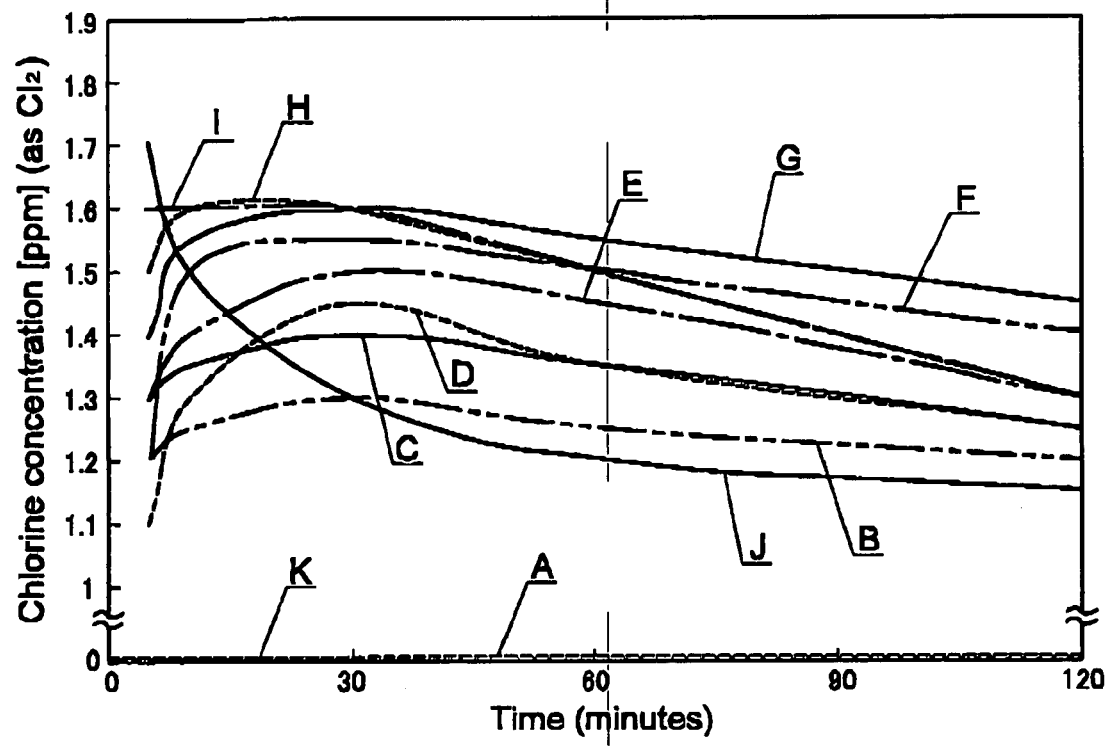
FIG. 2 is a graph showing the change over time in combined content of free residual bromine and chlorine dioxide for each of the tests.

The invention claimed is:

1. A method of forming at least either a hypobromous acid or a water-soluble salt thereof by adding at least either a hypochlorous acid or a water-soluble salt thereof, a bromide and tetrachlorodecaoxide to a liquid, and reacting in the liquid, wherein the molar ratio of the bromide to tetracholorodecaoxide is 1:0.002 to 0.3.

2. The method according to claim 1, wherein a mixed solution of the bromide and tetrachlorodecaoxide pre-mixed in water and the at least either hypobromous acid or water-soluble salt thereof are separately added to the liquid.

3. The method according to claim 1, wherein a mixed solution of the bromide and tetrachlorodecaoxide pre-mixed in water and the at least either hypobromous acid or water-soluble salt thereof are separately added to the liquid.

4. The method according to claim 1, wherein the liquid to be treated is selected from the group consisting of process water of a pulp and paper mill, industrial circulating cooling water, and hot spring water.

\* \* \* \* \*

UNITED STATES PATENT AND TRADEMARK OFFICE
CERTIFICATE OF CORRECTION

PATENT NO. : 7,785,559 B2
APPLICATION NO. : 11/662120
DATED : August 31, 2010
INVENTOR(S) : Nishi et al.

It is certified that error appears in the above-identified patent and that said Letters Patent is hereby corrected as shown below:

Column 22, lines 1-2, Claim 4, "liquid to be treated is selected" should read -- liquid is selected --

Signed and Sealed this

Fourteenth Day of December, 2010

David J. Kappos
*Director of the United States Patent and Trademark Office*